United States Patent
Coulter et al.

(10) Patent No.: US 10,722,597 B2
(45) Date of Patent: Jul. 28, 2020

(54) CYCLODEXTRIN-PANOBINOSTAT ADDUCT

(71) Applicant: MIDATECH LTD., Abington Oxford Oxfordshire (GB)

(72) Inventors: Tom Coulter, Oxford (GB); Stephen Damment, Oxford (GB); Alessandro Pace, Oxford (GB); Daniel Palmer, Oxford (GB)

(73) Assignee: MIDATECH LTD., Oxford (GB)

( * ) Notice: Subject to any disclaimer, the term of this patent is extended or adjusted under 35 U.S.C. 154(b) by 0 days.

(21) Appl. No.: 16/081,694

(22) PCT Filed: Mar. 29, 2017

(86) PCT No.: PCT/EP2017/057472
§ 371 (c)(1),
(2) Date: Aug. 31, 2018

(87) PCT Pub. No.: WO2017/167837
PCT Pub. Date: Oct. 5, 2017

(65) Prior Publication Data
US 2019/0151468 A1    May 23, 2019

(30) Foreign Application Priority Data

Mar. 31, 2016 (GB) .................................. 1605406.6
Jun. 15, 2016 (GB) .................................. 1610440.8

(51) Int. Cl.
| | | |
|---|---|---|
| A61K 47/69 | (2017.01) |
| A61K 31/4045 | (2006.01) |
| A61K 47/40 | (2006.01) |
| C08B 37/16 | (2006.01) |
| A61K 9/08 | (2006.01) |
| A61K 9/19 | (2006.01) |
| A61K 47/14 | (2017.01) |
| A61M 5/142 | (2006.01) |

(52) U.S. Cl.
CPC ............ *A61K 47/6951* (2017.08); *A61K 9/08* (2013.01); *A61K 9/19* (2013.01); *A61K 31/4045* (2013.01); *A61K 47/14* (2013.01); *A61K 47/40* (2013.01); *A61M 5/14276* (2013.01); *C08B 37/0015* (2013.01)

(58) Field of Classification Search
CPC .......... A61K 47/6951; A61K 9/19; A61K 9/08
See application file for complete search history.

(56) References Cited

U.S. PATENT DOCUMENTS

| | | |
|---|---|---|
| 8,835,501 B2 | 9/2014 | Bastin et al. |
| 2003/0216475 A1 | 11/2003 | Asakawa et al. |
| 2017/0216256 A1 | 8/2017 | Gill |

FOREIGN PATENT DOCUMENTS

| | | | |
|---|---|---|---|
| WO | 2008/002862 | 1/2008 | |
| WO | 2008/090585 | 7/2008 | |
| WO | 2009/039226 | 3/2009 | |
| WO | WO2009039226 A1 * | 3/2009 | ............... A61K 9/19 |
| WO | WO 2013/135727 | 9/2013 | |
| WO | 2015/191931 | 12/2015 | |

OTHER PUBLICATIONS

Zhou, Jiangbing, et al., (2012) "Novel Delivery Strategies for Glioblastoma", Cancer J., 18(1):1-22.

* cited by examiner

*Primary Examiner* — Pancham Bakshi
(74) *Attorney, Agent, or Firm* — Carol L. Francis; Rudy J. Ng; Bozicevic, Field & Francis LLP (57) ABSTRACT

The present invention provides a method for producing a cyclodextrin-panobinostat adduct, comprising: a) providing a first aqueous solution comprising a buffering agent, the solution having a pH in the range 2.0 to 4.0; b) dissolving panobinostat in said first aqueous solution to provide a second aqueous solution; and c) mixing said second aqueous solution comprising panobinostat with a third aqueous solution comprising a cyclodextrin to form a fourth aqueous solution comprising a cyclodextrin-panobinostat adduct. Also provided is an artificial cerebrospinal fluid (CSF) solution comprising the cyclodextrin-panobinostat adduct and medical uses of the cyclodextrin-panobinostat adduct, including in the treatment of brain tumours.

13 Claims, 8 Drawing Sheets

CYCLODEXTRIN-PANOBINOSTAT ADDUCT

FIELD OF THE INVENTION

The present invention relates to pharmaceutical formulations of a histone deacetylase (HDAC) inhibitor, methods for producing such formulations and uses of the formulations in the treatment of brain tumours, particularly glioma.

BACKGROUND TO THE INVENTION

The present invention is directed at pharmaceutical compositions and formulations, and methods of making and administering such compositions and products, for use in the treatment of brain tumours, including glioma such as diffuse intrinsic pontine glioma (DIPG).

Histone deacetylase (HDAC) inhibitors show significant potential for the treatment of various cancers. Panobinostat (Farydak®, LBH-589, 2-(E)-N-hydroxy-3-[4[[[2-(2-methyl-1H-indol-3-yl)ethyl]amino]methyl]phenyl]-2-propenamide) is a non-selective HDAC inhibitor used in the treatment of multiple myeloma. Combination therapy of panobinostat and radiation has been proposed for the treatment of solid tumours (WO2007/050655). However, hydroxamate compounds, including panobinostat, exhibit poor aqueous solubility and stability (WO2009/039226). Panobinostat formulations have been proposed that employ at least one alcohol to reduce oxidation and hydrolysis (WO2008/086330).

Wehrmann et al., *PLOS ONE*, 2012, Vol. 7, Issue 10, e48561, describe lowering of intracellular cholesterol levels in Niemann-Pick Type C Fibroblasts by vorinostat, panobinostat, beta-cyclodextrin and combinations thereof.

Grasso et al., *Nature Medicine*, 2015, Vol. 21, No. 6, pp. 555-559, report that the multi-histone deacetylase inhibitor, panobinostat, demonstrated therapeutic efficacy both in vitro and in DIPG orthotopic xenograft models. However, panobinostat was formulated in dimethyl sulphoxide (DMSO) for convection-enhanced delivery (CED) to the xenograft tumour-bearing mice. DMSO is a mild oxidising agent and has a number of shortcomings for clinical use in humans.

WO2015/191931 describes pharmaceutical compositions containing a hydrophobic drug (which may be an HDAC inhibitor), prodrug thereof, salt thereof, isoform thereof, or a combination thereof; cyclodextrin, prodrug thereof, salt thereof, of combination thereof; polyethylene glycol, propylene glycol, or combination thereof; and a pharmaceutically acceptable carrier, as well as medical uses thereof, including in the treatment of a brain disease.

WO2008/002862 describes pharmaceutical compositions containing inhibitors of histone deacetylase and B vitamins and medical uses thereof, including in the treatment of proliferative disorders.

Hockly et al., PNAS, 2003, Vol. 100(4), pp. 2041-2046, describes treatment of a mouse model of Huntington's disease using the HDAC inhibitor suberoylanilide hydroxamic acid (SAHA), administered orally.

US2013177499 proposes use of bacterially derived minicells as delivery vehicles for active agents against brain tumours.

WO2013/135727 describes a method for treatment of glioma by convection enhanced delivery (CED) using a composition of carboplatin in artificial cerebrospinal fluid (CSF).

There remains an unmet need for pharmaceutical formulations that are stable and amenable to central administration (e.g. via CED) for the treatment of brain tumours, including glioma. The present invention addresses these and other needs.

BRIEF DESCRIPTION OF THE INVENTION

Broadly, the present invention relates to compositions and formulations of the HDAC inhibitor, panobinostat, that are suitable for administration to the brain via convection-enhanced delivery (CED). The present inventors have surprisingly found that a "pH bridging" method provides a convenient route to produce a water soluble, stable complex or adduct of 2-hydroxypropyl-β-cyclodextrin and panobinostat. The 2-hydroxypropyl-β-cyclodextrin-panobinostat adduct has, in turn, been found to be soluble in artificial cerebrospinal fluid (CSF). As described in the examples herein, the cyclodextrin-panobinostat adduct exhibits excellent HDAC inhibitory activity, in vitro tumour cell killing activity and, in preliminary human clinical studies, potential in vivo therapeutic activity against Diffuse Intrinsic Pontine Glioma (DIPG). A particular advantage of the method of production and cyclodextrin-panobinostat adduct of the present invention is that these avoid undesirable agents such as dimethyl sulphoxide (DMSO). DMSO, especially at high concentrations, is undesirable in pharmaceuticals for human use and is a mild oxidising agent that could negatively affect the stability of panobinostat.

Accordingly, in a first aspect the present invention provides a method for producing a cyclodextrin-panobinostat adduct, comprising:
  a) providing a first aqueous solution comprising a buffering agent, the solution having a pH in the range 2.0 to 4.0;
  b) dissolving panobinostat in said first aqueous solution to provide a second aqueous solution; and
  c) mixing said second aqueous solution comprising panobinostat with a third aqueous solution comprising a cyclodextrin to form a fourth aqueous solution comprising a cyclodextrin-panobinostat adduct.

The cyclodextrin may be any cyclodextrin suitable for pharmaceutical use, e.g. an alpha-, beta- or gamma-cyclodextrin. In particular cases, the cyclodextrin is a beta-cyclodextrin. Preferably, the cyclodextrin is 2-hydroxypropyl-β-cyclodextrin.

The buffering agent may comprise any pharmaceutically acceptable acid (and its conjugate base). Preferably, the buffering agent comprises citric acid and citrate, for example citric acid and sodium citrate. The concentration of the buffering agent may be in the range 0.01M to 1M, e.g. 0.1M.

The pH of the first aqueous solution is in the range 2.0 to 4.0, for example 2.5 to 3.5. Preferably, the pH of the first aqueous solution is about 3.0. At this pH panobinostat free base exhibits good aqueous solubility. Indeed, the concentration of panobinostat in the second aqueous solution is in the range 1 mM to 20 mM. For example, panobinostat free base is soluble at 10 mM concentration in citrate buffer at pH 3.0. The step of dissolving panobinostat in the first aqueous solution may involve shaking and/or mixing for a period of between 1 minute and 20 minutes, e.g. for 10 minutes.

In some cases, the concentration of cyclodextrin (e.g. 2-hydroxypropyl-β-cyclodextrin) in said third aqueous solution may be in the range 10 mg/mL to 200 mg/mL. For example, the third solution may be 100 mg/mL 2-hydroxypropyl-β-cyclodextrin in water.

In some cases, the method of the first aspect of the invention further comprises:

d) adding a sufficient quantity of a base to said fourth aqueous solution comprising the cyclodextrin-panobinostat adduct in order to provide a fifth aqueous solution having a pH in the range 6.0 to 8.0.

In some cases, the method of the first aspect of the invention further comprises drying said fifth aqueous solution to form a solid comprising said cyclodextrin-panobinostat adduct. In this way the dried solid (e.g. lyophilised cake) has pH around neutral for readiness for reconstitution to or close to neutral pH.

In some cases, the method of the first aspect of the invention further comprises drying said fourth aqueous solution to form a solid comprising said cyclodextrin-panobinostat adduct. In this way the dried solid (e.g. lyophilised cake) has a relatively acidic pH, which may or may not be adjusted, e.g. to or towards neutral pH (around 7) before, during or after any reconstitution, rehydrating or dissolving step.

In either case (i.e. drying the fifth or the fourth aqueous solution), said drying may comprise freeze-drying (lyophilising) under reduced pressure to form a lyophilised solid comprising said cyclodextrin-panobinostat adduct. Suitable freeze-drying conditions include: cooling to −52° C. under a vacuum (0.053 mbar) for around 2 hrs. However, it will be appreciated that a variety of techniques and conditions for freeze-drying/lyophilisation are known and which would find ready use in the drying step(s) contemplated herein. Generally speaking, lyophilisation comprises a freezing step, in which the solution is cooled until all components in the solution are frozen. This may comprise lowering the temperature to below −40° C., such as below −50° C. Following freezing there is a primary drying step. In the primary drying step ice formed during freezing is removed by sublimation. The primary drying step may be carried out at a reduced pressure, such as <10 mbar (1 kPa), or <0.1 mbar (10 Pa). The primary drying step may be carried out at a temperature greater than the temperature used for the freezing step. The primary drying step may be followed by a secondary drying step. The temperature of the secondary drying step may be higher than the temperature of the primary drying step. The lyophilisation may in some cases take more than 1 hour, e.g. 2 or 3 hours or even longer.

In some cases the solution is dried to a lyophilised solid, e.g. a cake, powder or granular mass, having a water content of less than 10% w/w, optionally less than 5% w/w. The lyophilised solid may be a pharmaceutically acceptable solid, e.g. a pharmaceutically acceptable cake.

In some cases, the method of this aspect of the invention further comprising reconstituting the dried solid, e.g. lyophilised solid, comprising the cyclodextrin-panobinostat adduct by dissolving in a reconstitution solution. The reconstitution solution is preferably a pharmaceutically acceptable solution in which the cyclodextrin-panobinostat adduct is soluble. In particular, the reconstitution solution may be selected from the group consisting of: artificial cerebrospinal fluid (CSF), Ringer's solution, water for injection (WFI), and a buffered salt solution. In certain cases, for example when administration to the central nervous system (CNS) is intended, the reconstitution solution may comprise artificial CSF.

In some cases, there may be a considerable delay between the freeze-drying step and the subsequent reconstitution step. The lyophilised solid comprising the cyclodextrin-panobinostat adduct may exhibit good stability leading to significant shelf-life. The stability and/or relative compactness of the lyophilised solid in comparison to the corresponding aqueous solution makes the lyophilised solid attractive for storage and/or shipping. The reconstitution step may be carried out immediately prior to administration to a patient. In some cases, reconstitution may be carried out up to 24, 48 or 72 hours before administration to a patient. By carrying out reconstitution close to the time of administration, there is less chance that one or more of the salts forming the artificial CSF solution will crystallise as a result of cyclodextrin-effected nucleation or other nucleation event.

In some cases, the method further comprises adjusting the pH of the solution before, during or after reconstitution. Particularly where the cyclodextrin-panobinostat adduct is freeze-dried without first neutralising the pH (i.e. where the fourth aqueous solution is dried), it may be necessary to add adjust the pH, for example by adding sufficient quantity of a base to bring the pH into the range 6.0 to 8.0.

In some cases, the method of this aspect of the invention further comprises mixing the fifth aqueous solution comprising the cyclodextrin-panobinostat adduct with an artificial cerebrospinal fluid (CSF) solution to provide a sixth aqueous solution comprising the cyclodextrin-panobinostat adduct in artificial CSF.

In some cases, the concentration of panobinostat in artificial CSF (whether the sixth aqueous solution or solid reconstituted into artificial CSF) is in the range 1 µM to 100 µM, e.g. 1 µM to 20 µM. This concentration range is thought to correspond to the efficacious anti-tumour concentration of the drug. The sixth aqueous solution, or the freeze-dried solid comprising the cyclodextrin-panobinostat adduct reconstituted in artificial CSF, may conveniently be the solution for administration to a patient to be treated, e.g. a person or other mammal suffering from or suspected to have a glioma.

In some case, the method of the first aspect of the invention further comprises a step of filtering and/or sterilizing at least one of said solutions and/or the freeze-dried solid comprising the cyclodextrin-panobinostat adduct. Typically, the method may involve sterile filtering the sixth aqueous solution or the solution formed by reconstituting the freeze-dried solid comprising the cyclodextrin-panobinostat adduct in artificial CSF, e.g. in readiness for therapeutic administration.

In some cases, the method further comprises introducing at least a portion of the sixth aqueous solution or the solution formed by reconstituting the freeze-dried solid comprising the cyclodextrin-panobinostat adduct in artificial CSF into at least one convection-enhanced delivery (CED) catheter. The CED catheter or catheters may be microcatheters for implantation (or pre-implanted) in the head of a patient to be treated.

In a second aspect, the present invention provides a cyclodextrin-panobinostat adduct produced or producible by a method of the first aspect of the invention.

It has been reported that cyclodextrin complexes may take the form of nanoparticles (see, e.g., He et al., *Micron*, 2008, Vol. 39, pp. 495-516). Indeed, atomic force microscopy (AFM) and electron microscopy studies indicate that cyclodextins, including β-cyclodextrins, form concentration-dependent aggregates in solution, having a hydrodynamic radius of around 60 nm. Accordingly, the cyclodextrin-panobinostat adduct of the second aspect of the invention may, in some cases, take the form of a nanoparticle or a nanotube. In particular, the cyclodextrin-panobinostat adduct may be in the form of a nanoparticle having a diameter in the range 10 nm to 500 nm, e.g. 10 nm to 100 nm or even 50 nm to 100 nm. The nanoparticles and/or nanotubes may be self-assembled (e.g. in solution). The nanoparticles and/or nanotubes may be reversible, e.g., forming monomeric cyclodextrin-panobinostat adducts in solution. In some cases the nanoparticle and/or nanotube self-assembly and reversal may be concentration and/or temperature dependent.

In a third aspect, the present invention provides an artificial cerebrospinal fluid (CSF) solution comprising a cyclodextrin-panobinostat adduct, e.g. the cyclodextrin-panobinostat adduct of the second aspect of the invention. The artificial CSF solution may be produced or may be producible by a method of the first aspect of the invention. In some cases, the cyclodextrin-panobinostat adduct is 2-hydroxypropyl-β-cyclodextrin-panobinostat.

Preferably, the cyclodextrin-panobinostat adduct of the second aspect of the invention and/or the artificial cerebrospinal fluid (CSF) solution of the third aspect of the invention comprising a cyclodextrin-panobinostat adduct is substantially free of dimethyl sulphoxide (DMSO). In particular, the solution may have a concentration of DMSO (v/v) of less than 1000 parts per million (ppm), e.g. less than 100, less than 10 or even less than 1 ppm.

In particular, the cyclodextrin-panobinostat adduct of the second aspect of the invention and/or the artificial cerebrospinal fluid (CSF) solution of the third aspect of the invention may be substantially free of an organic solvent (for example, acetone, tetrahydrofuran, dichloromethane, acetonitrile, dimethylformamide and DMSO). For example, the solution may have a concentration of an organic solvent or a total concentration of any organic solvent (v/v) of less than 1000 parts per million (ppm), e.g. less than 100, less than 10 or even less than 1 ppm.

In a fourth aspect, the present invention provides a convection-enhanced delivery (CED) catheter comprising the artificial CSF solution of the third aspect of the invention.

In a fifth aspect, the present invention provides an artificial cerebrospinal fluid (CSF) solution of the third aspect of the invention or a cyclodextrin-panobinostat adduct of the second aspect of the invention for use in medicine.

In a sixth aspect, the present invention provides an artificial cerebrospinal fluid (CSF) solution of the third aspect of the invention or a cyclodextrin-panobinostat adduct of the second aspect of the invention for use in a method of treatment of a brain tumour in a mammalian subject.

In some cases, the brain tumour may comprise a glioma, such as a brainstem glioma, an astrocytoma (e.g. glioblastoma multiforme), an oligodendroglioma, an oligoastrocytoma or a Diffuse Intrinsic Pontine Glioma (DIPG).

In some cases, the method of treatment comprises administration of the artificial CSF solution to the brain of said mammalian subject via convection-enhanced delivery (CED).

In a seventh aspect, the present invention provides a method of treatment of a brain tumour in a mammalian subject, comprising administering a therapeutically effective amount of an artificial cerebrospinal fluid (CSF) solution of the third aspect of the invention or a cyclodextrin-panobinostat adduct of the second aspect of the invention to a mammalian subject in need thereof.

In some cases, the brain tumour may comprise a glioma, such as a brainstem glioma, an astrocytoma (e.g. glioblastoma multiforme), an oligodendroglioma, an oligoastrocytoma or a Diffuse Intrinsic Pontine Glioma (DIPG).

In some cases the method comprises administration of the artificial CSF solution to the brain of said mammalian subject via convection-enhanced delivery (CED).

In accordance with the present invention, the subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human. The subject may in certain cases, particularly if the tumour is a DIPG tumour, be a human child, e.g. under 10 years of age (such as 1 to 5 years of age).

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 1 shows MTT-assessed cell viability (%) plotted against drug concentration (μM) for A) HP-β-CD panobinostat (squares), cyclodextrin (triangles) and artificial CSF (circles) against U87MG cells after 72 hours treatment; B) HP-β-CD panobinostat (squares), cyclodextrin (triangles) and artificial CSF (circles) against U87MG cells after 48 hours treatment; C) HP-β-CD panobinostat (squares), cyclodextrin (triangles) and artificial CSF (circles) against HEPG2 cells after 72 hours treatment; and D) HP-β-CD panobinostat against U87MG (circles), HEPG2 (diamonds) and h19 (triangles) cells after 72 hours treatment. Error bars indicate plus or minus standard deviation of triplicate samples. N=1 experimental replicate.

FIG. 2 shows A) cell viability (%) of SF8628 DIPG cells plotted against HP-β-CD panobinostat concentration (μM) following 72 hours treatment; B) cell viability (% live cells) plotted against $\log_{10}$ dose of HP-β-CD panobinostat concentration following 72 hours treatment (circles), 6 hours treatment (squares) and 30 minutes treatment (diamonds). Error bars indicate plus or minus standard deviation of triplicate samples.

DETAILED DESCRIPTION OF THE INVENTION

In describing the present invention, the following terms will be employed, and are intended to be defined as indicated below.

"Panobinostat" (Farydak®, LBH-589, 2-(E)-N-hydroxy-3-[4[[[2-(2-methyl-1H-indol-3-yl)ethyl]amino]methyl]phenyl]-2-propenamide) is a non-selective HDAC inhibitor having the chemical structure depicted below:

As used herein, unless context specifies otherwise (such as when described as "free base panobinostat"), "panobinostat" includes salt forms (e.g. panobinostat citrate, panobinostat lactate, and the like). Methods for producing hydroxamate derivatives useful as deacetylase inhibitors, including panobinostat, are detailed in WO2002/022577, the entire content of which is expressly incorporated herein by reference.

"Cyclodextrin" is a cyclic oligosaccharide and specifically includes α-cyclodextrins, β-cyclodextrins, and γ-cyclodextrins. The cyclodextrin is typically a pharmaceutically acceptable cyclodextrin. In particular cases, the cyclodextrin is 2-hydroxypropyl-β-cyclodextrin.

"Convection-enhanced delivery (CED)" is a method of delivering a drug directly to the brain through one or more very small catheters which are surgically placed into or around the brain tumour. The placement of the catheters may be stereotactically directed, e.g. to minimize off-target effects. WO2013/135727, the entire content of which is expressly incorporated herein by reference, describes a method for treatment of glioma by convection enhanced delivery (CED) using a composition of carboplatin in artificial cerebrospinal fluid (CSF). CED typically employs in-line sterilising filters. A number of sterilising filters are not compatible with DMSO (for example, cellulose acetate; cellulose nitrate; polycarbonate; polyether sulfone; Sartobran P; some PVDFs; PVC; Metricet; Nylon; and PES). It is therefore desirable that the panobinostat artificial CSF formulation for CED delivery should be substantially free from certain organic solvents such as DMSO. The use of cyclodextrin-panobinostat of the present invention in a formulation for CED delivery is therefore advantageous in the context of commonly used in-line sterilising filters.

"Artificial Cerebrospinal Fluid (CSF)"

Artificial cerebrospinal fluid (CSF) is intended to match the electrolyte concentrations of CSF. Preferably, artificial CSF is prepared from high purity water and analytical grade reagents or can be obtained from medical and commercial suppliers (e.g. South Devon Healthcare NHS Foundation Trust, UK or Tocris Bioscience, Bristol, UK). The final ion concentrations in artificial CSF may be as follows (in mM):
Na 150;
K 3.0;
Ca 1.4;
Mg 0.8;
P 1.0;
Cl 155.

Optionally, each ionic constituent may be at a concentration plus or minus (±) 10%, ±5%, ±2%, ±1% or ±0.5% from the above-listed concentration values. Further optionally, the artificial CSF may further comprise glucose and/or one or more proteins at concentrations typically found in human CSF. In preferred cases, the artificial CSF does not comprise glucose or protein.

The following is presented by way of example and is not to be construed as a limitation to the scope of the claims.

EXAMPLES

Example 1—Procedure for Production of Panobinostat-2-Hydroxypropyl-β-Cyclodextrin Adduct Panobinostat free base is poorly soluble in water. It is similarly insoluble in concentrated aqueous solutions of 2-hydroxypropyl-β-cyclodextrin (HP-β-CD) (450 mg/ml). However, Panobinostat is soluble in citrate buffer at pH 3.0.

Solution A: 0.1M Citric Acid in Water
Citric acid (Sigma Aldrich C-0759; Lot #21K0042) (2.101 g) was weighed out and dissolved in 100 mL ultrapure water.

Solution B: 0.1M Sodium Citrate in Water
Sodium citrate (tribasic) (Sigma Aldrich C3434; Lot #1304640/41807230 (2.944 g) was weighed out and dissolved in 100 mL ultrapure water.

Solution C: 0.1M Citrate Buffer
Solution A (82 mL) and solution B (18 mL) were added to a 250 mL Duran flask and mixed briefly to form [C]. The pH of the citrate buffer was measured and found to be pH3.0.

Solution D: 10 mM Panobinostat Solution in Citrate Buffer (25 mL)
Concentration=10 mM=0.01M
Volume=25 mL=0.025 L
Therefore number of moles required=$2.5 \times 10^{-4}$
Molecular weight of Panobinostat=349.43 g/mol
Therefore mass of Panobinostat required=82.36 mg
Thus, Panobinostat free base (81.0 mg) was weighed out and dissolved in solution C (24.59 mL).

The mixture was shaken on an orbital shaker for 10 minutes to give a clear, colourless solution [D].

Solution E: 100 mg/mL 2-Hydroxypropyl-β-Cyclodextrin in Water (20 mL)

2-Hydroxypropyl-β-cyclodextrin has an average molecular weight of 1460 g/mol. For simplicity it was prepared as follows.
Concentration=100 mg/mL.
2-Hydroxypropyl-β-cyclodextrin (Sigma Aldrich H107; Lot #048K0672) (2.004 g) was weighed out and dissolved in 20.04 mL ultrapure water. The mixture was shaken on an orbital shaker for 10 minutes to give a clear, colourless solution [E].

Solution F: Panobinostat—2-Hydroxypropyl-β-Cyclodextrin Adduct (5 mM)

Equal volumes of solutions D (2 mL) and E (2 mL) were mixed in a Falcon tube. The clear, colourless solution was vortexed briefly to homogenise.

Solution G: Panobinostat—2-Hydroxypropyl-β-Cyclodextrin Adduct (3.125 mM)

To produce a neutral solution (~pH7) for injection, a sample of [F] (1 mL) was mixed with $NaOH_{(aq)}$ (0.6 mL, 0.2M) to give a clear, colourless solution (1.6 mL in volume).

Solution H: Sterile Solution of Panobinostat—2-Hydroxypropyl-β-Cyclodextrin Adduct in aCSF (Artificial Cerebrospinal Fluid) (10 μM)

aCSF Part 1 solution (South Devon Healthcare; Lot #1407292) (155.5 mL) was added to a 250 mL Duran flask. Solution [G] (0.5 mL) was then added via pipette to give a final solution of Panobinostat in aCSF at concentration 10 μM. The solution was briefly mixed and then filter sterilised in a laminar flow hood using a SteriFlip sterile filter cartridge. The clear, colourless solution was then stored at 4° C.

Example 2—HDAC Enzyme Assays

The inhibitory activity of panobinostat dissolved in DMSO and that of the HP-β-CD panobinostat adduct (prepared as described in Example 1) were compared against HDAC types 1-11. Both were tested in singlicate 10-dose $IC_{50}$ mode with 3-fold serial dilution starting at 10 μM against 11 HDACs. HDAC reference compounds, Trichostatin A ((R,2E,4E)-6-(4-(dimethylamino)benzoyl)-N-hydroxy-4-methylhepta-2,4-dienamide) and TMP 269 (N-((4-(4-phenylthiazol-2-yl)tetrahydro-2H-pyran-4-yl)methyl)-3-(5-(trifluoromethyl)-1,2,4-oxadiazol-3-yl)benzamide), were tested in a 10-dose $IC_{50}$ with 3-fold serial dilution started at 10 μM.

The substrates were as follows:
Substrate for HDAC 1, 2, 3, 6, 10: Fluorogenic peptide from p53 residues 379-382 (RHKK(Ac)AMC)
Substrate for HDAC 4, 5, 7, 9 and 11: Fluorogenic HDAC Class2a
Substrate (Trifluoroacetyl Lysine)
Substrate for HDAC 8: Fluorogenic peptide from p53 residues 379-382 (RHK(Ac)K(Ac)AMC)

$IC_{50}$ values were calculated using the GraphPad Prism 4 program based on a sigmoidal dose-response equation. The blank (DMSO) value was entered as 1.00E-012 of concentration for curve fitting.

The $IC_{50}$ values for each compound against each HDAC enzyme are shown below.

| Compound ID | HDAC1 IC50 (M) | HDAC2 IC50 (M) | HDAC3 IC50 (M) | HDAC4 IC50 (M) |
|---|---|---|---|---|
| HP-β-CD Panobinostat | 8.65E-09 | 1.59E-08 | 4.02E-09 | 5.67E-07 |
| Panobinostat in DMSO | 1.61E-09 | 4.97E-09 | 7.51E-10 | 1.55E-06 |
| Trichostatin A | 1.05E-08 | 8.83E-09 | 9.33E-09 | ND |
| TMP 269 | ND | ND | ND | 3.76E-07 |

| Compound ID | HDAC5 IC50 (M) | HDAC6 IC50 (M) | HDAC7 IC50 (M) | HDAC8 IC50 (M) |
|---|---|---|---|---|
| HP-β-CD Panobinostat | 1.10E-07 | 7.49E-09 | 1.82E-06 | 5.57E-08 |
| Panobinostat in DMSO | 1.66E-07 | 1.77E-09 | 3.68E-06 | 5.19E-08 |
| Trichostatin A | ND | 1.41E-09 | ND | 3.66E-07 |
| TMP 269 | 3.54E-07 | ND | 1.53E-07 | ND |

| Compound ID | HDAC9 IC50 (M) | HDAC10 IC50 (M) | HDAC11 IC50 (M) |
|---|---|---|---|
| HP-β-CD Panobinostat | 9.27E-07 | 2.03E-08 | 1.38E-06 |
| Panobinostat in DMSO | 1.04E-06 | 1.27E-08 | 1.67E-06 |
| Trichostatin A | ND | 3.96E-08 | 7.89E-06 |
| TMP 269 | 4.33E-08 | ND | ND |

ND indicates compound no tested against enzyme.

The results show that HP-β-CD panobinostat is equipotent to panobinostat in DMSO across the range of HDAC enzymes 1-11.

Example 3—In Vitro Cell Toxicity

Cytotoxicity of HP-β-CD panobinostat was assessed in Heptacellular Carcinoma and Glioblastoma.

U87MG (Glioblastoma) and HEPG2 (Hepatocellular carcinoma) cell lines were exposed to increasing doses of HP-β-CD panobinostat, Cyclodextrin alone or Artificial Cerebral Spinal Fluid (Artificial-CSF) alone for either 48 or 72 hrs. Cell viability was then assessed using MTT reagent.

The $IC_{50}$ of HP-β-CD panobinostat was determined to be approximately 0.01 μM (see FIGS. 1A-D). Cyclodextrin alone and artificial CSF alone were essentially non-toxic under the conditions tested.

Cytotoxcity of HP-β-CD panobinostat was assessed in human SF8628 DIPG cells (gift from Gupta group at UCSF, USA).

Figure 1A:
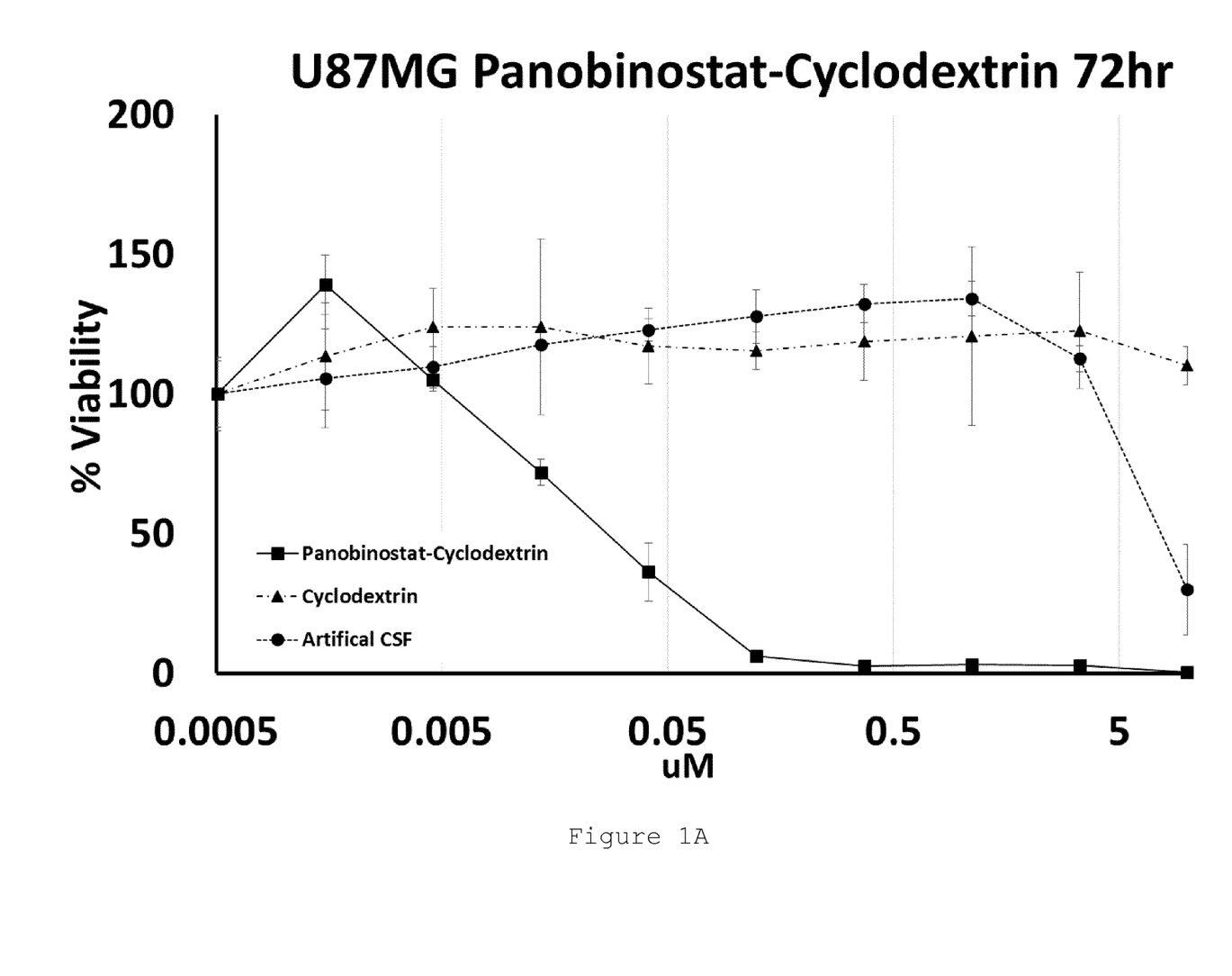
Figure 1B:
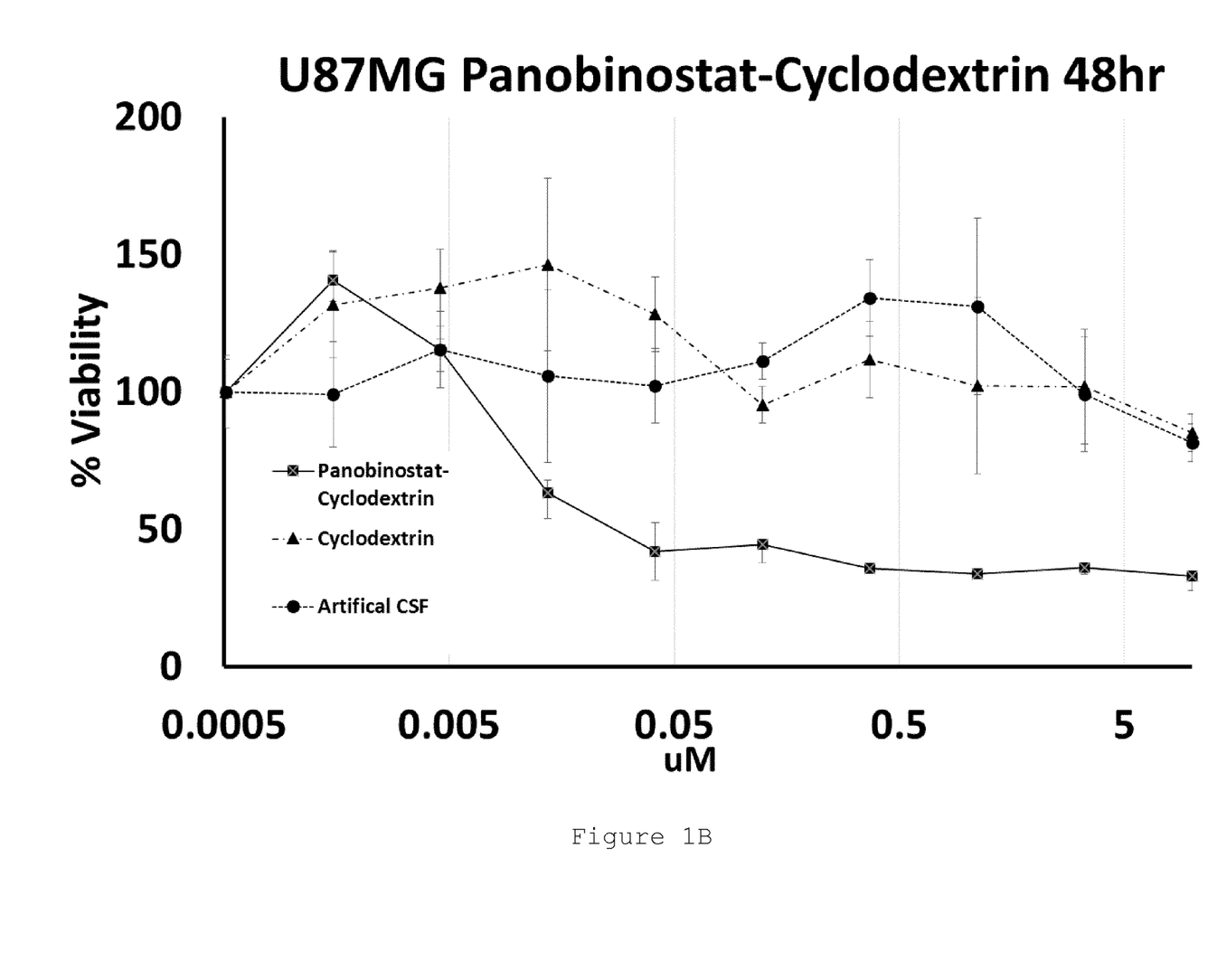
Figure 1C:
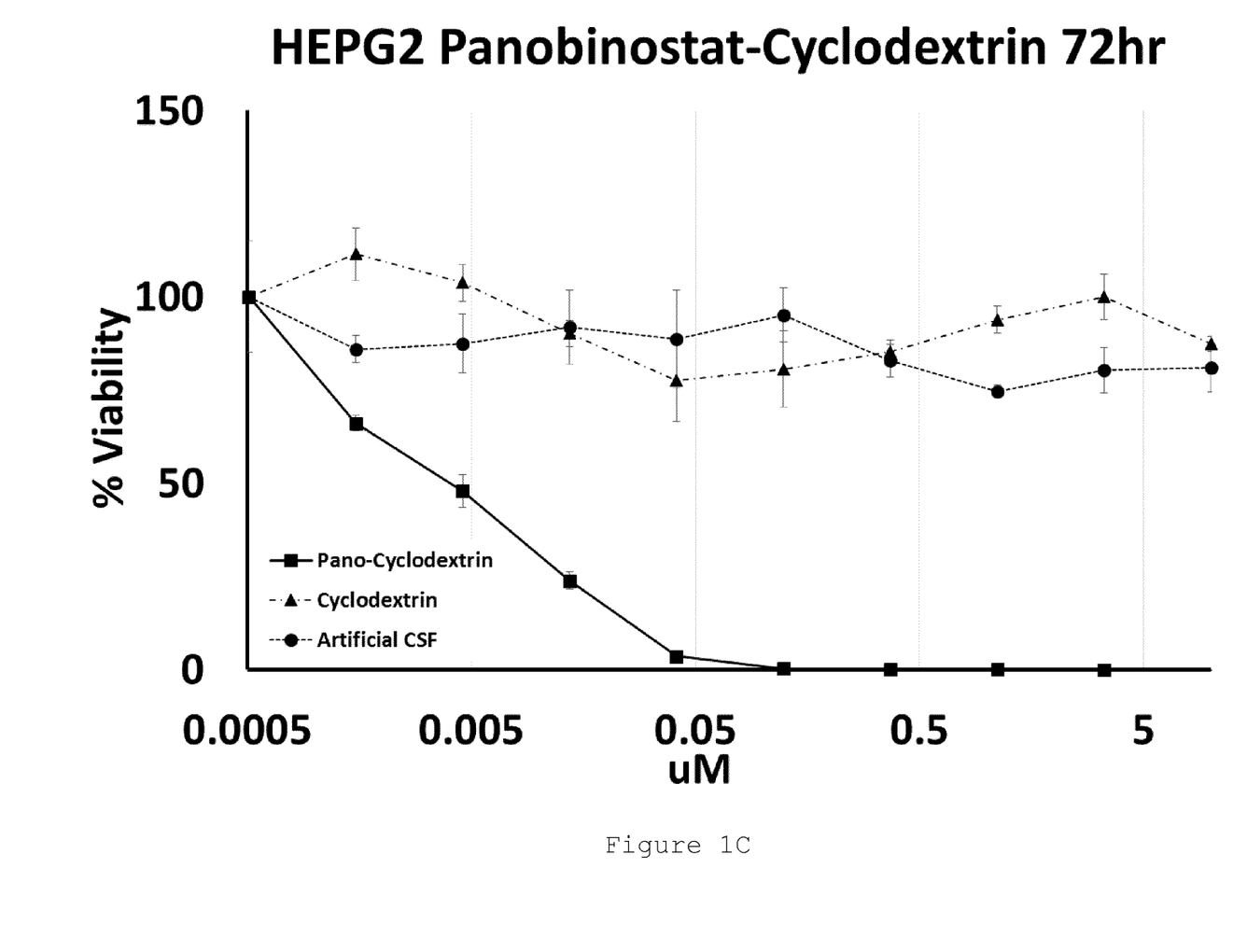
Figure 1D:
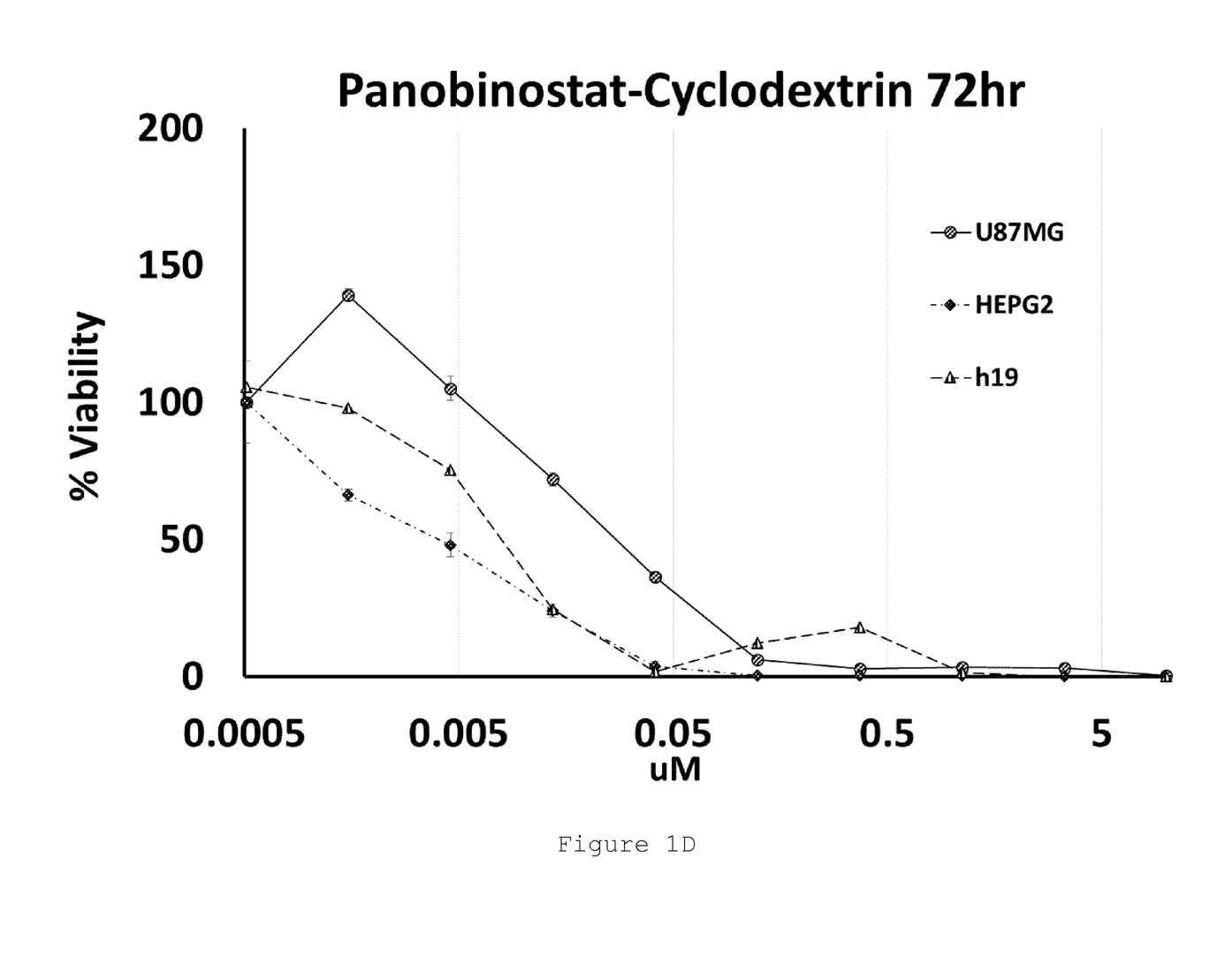
Figure 2A:
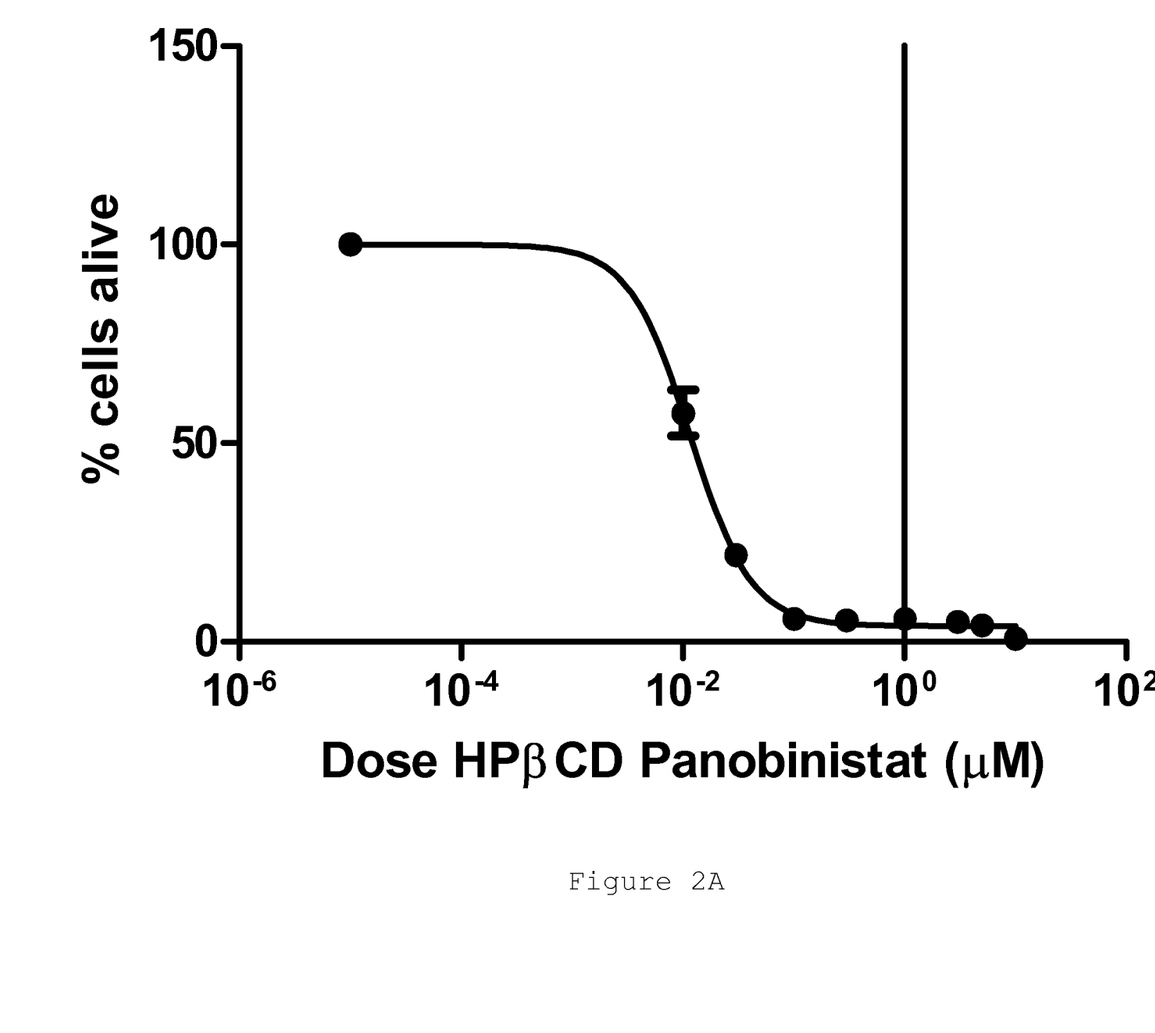

A fluorescent live-dead cell viability assay (Invitrogen) was employed. Cells cultured in presence of HP-β-CD panobinostat in artificial CSF for 72 hours at doses of 10 μM, 5 μM, 3 μM, 1 μM, 0.3 μM, 0.1 μM, 0.03 μM, and 0.01 μM in triplicate. The assay was repeated three times in three different passage. Cell viability compared to live and dead controls (& vehicle only control). The dose response curve was plotted using GraphPad Prism software (see FIG. 2A). The $IC_{50}$ value was calculated to be 0.01 μM.

These results demonstrate that panobinostat formulated as an HP-β-CD panobinostat adduct is soluble in artificial CSF at neutral pH and displays potent cancer cell killing activity against a range of tumour cell lines, including glioma and, in particular, DIPG cells in vitro.

Figure 2B:
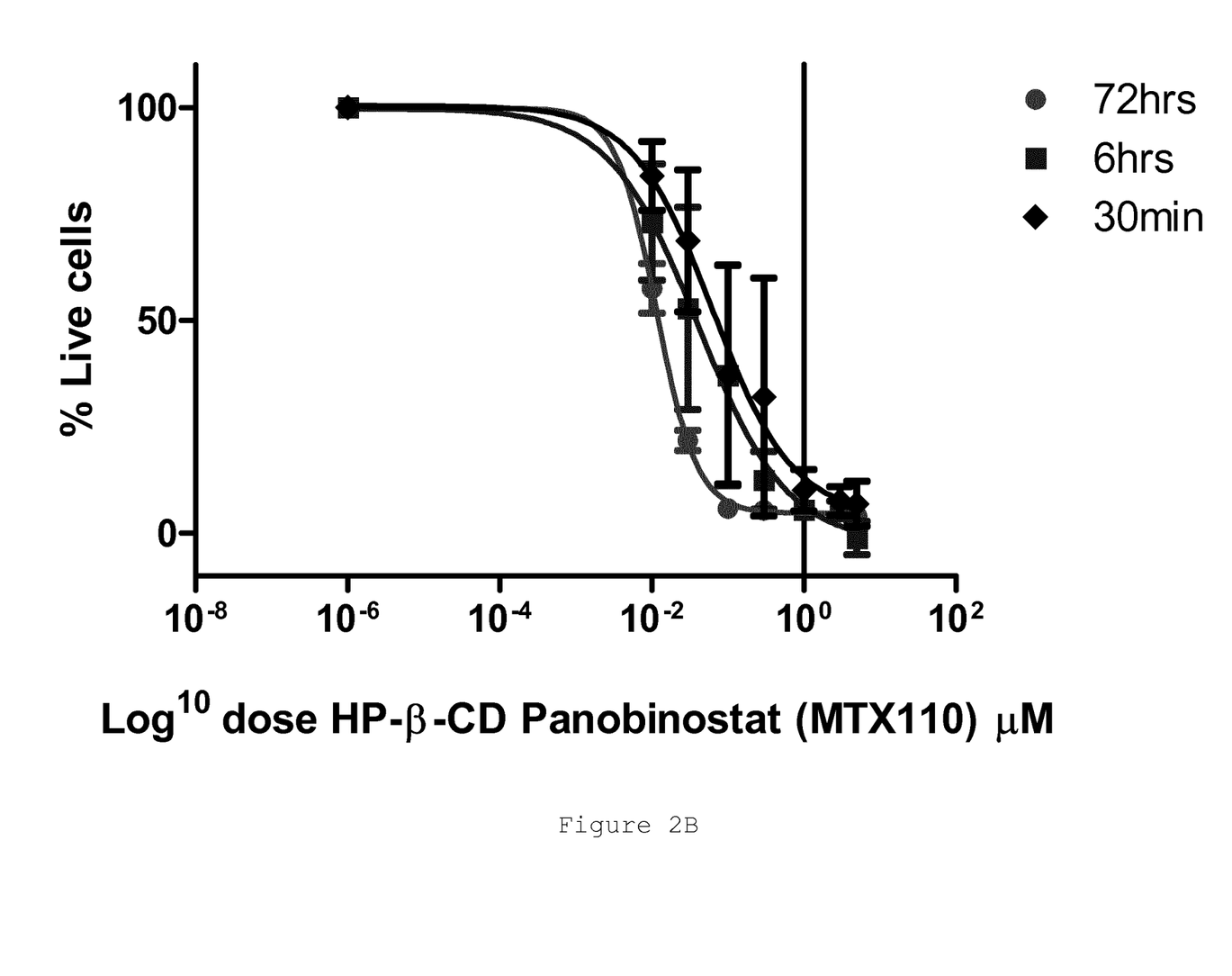

In order to investigate the time-course of HP-β-CD panobinostat action on DIPG cells, cells were cultured in presence of HP-β-CD panobinostat for 72 hours, 6 hours and 30 minutes at doses of 5 μM, 3 μM, 1 μM, 0.3 μM, 0.1 μM, 0.03 μM, 0.01 μM in triplicate, with three separate cell passage. Short time point incubation (6 hours and 30 minutes) assayed at 72 hours post dosing. The results are shown in FIG. 2B. $IC_{50}$ values are shown for each time point below:

| Incubation time | $IC_{50}$ (μM) |
|---|---|
| 72 hours | 0.01 |
| 6 hours | 0.04 |
| 30 minutes | 0.06 |

These results indicate that even brief exposure to cytotoxic concentrations may be sufficient for anti-tumour efficacy. Pharmacokinetic data suggest that HP-β-CD panobinostat in artificial CSF for CED-based delivery diffuses out from the catheter tip rapidly.

Example 4—Solubility and Stability of Panobinostat Formulations

From literature study, it has been identified that panobinostat may be dissolved in DMSO/water mixed phases. In order to administer the drug directly to the brain of a patient via the CED approach, filtered artificial cerebrospinal fluid (CSF) must be used as a diluent.

In the context of CED-based delivery, a drug solution is typically prepared on the day before the scheduled administration. If a patient is scheduled to receive a CED treatment on Monday, the drug solution would be prepared on Friday and stored in a refrigerator until Monday. Hence, a solution of panobinostat prepared in artificial CSF must be demonstrably stable for at least 48 hrs at 4° C.

This study aimed to determine the concentrations of panobinostat that can be successfully reached in DMSO/aCSF mixtures and their stability at 4° C. and room temperature.

A stock solution of panobinostat in DMSO was prepared at 70 mg/mL 0.2M=200 mM.

From this solution, a number of DMSO working solutions were prepared at 20 mM, 10 mM, 5 mM, 2 mM and 1 mM by dilution in DMSO.

These solutions were diluted 50:50 with artificial CSF (aCSF) and gave the following results.

| | After ½ dilution with aCSF to give . . . | | | | | |
|---|---|---|---|---|---|---|
| | 100 mM | 20 mM | 10 mM | 5 mM | 2 mM | 1 mM |
| Soluble/homogeneous | No | No | No | Yes | Yes | Yes |

The 20 mM solution was diluted further with aCSF to give the following concentrations. After mixing by vortex, samples were centrifuged for 60 seconds.

| 20 mM solution diluted with aCSF to give | 10 mM | 5 mM | 2 mM |
|---|---|---|---|
| Soluble/homogeneous | No (pellet) | No (pellet) | No (pellet) |

The 10 mM solution was diluted further with aCSF to give the following concentrations. After mixing by vortex, samples were centrifuged for 60 seconds.

| 20 mM solution diluted with aCSF to give | 5 mM | 2 mM | 1 mM | 0.5 mM |
|---|---|---|---|---|
| Soluble/homogeneous | Yes | No (pellet) | No (pellet) | No (pellet) |

It is apparent that the DMSO:aCSF ratio is important. Useful working concentrations can be prepared between 5 mM and 1 mM, but only if the DMSO ratio is ~50% v/v. For human in vivo use, presence of DMSO, particularly at a concentration as high as 50% v/v, is undesirable.

By comparison, the HP-β-CD panobinostat adduct is soluble and stable in artificial CSF at 4° C. for at least 48 hours.

Stock solutions of Panobinostat (10 mM) were made and dissolved in either DMSO or citrate buffer (pH 3). Samples were diluted to allow analysis by HPLC (to avoid overloading the system). Peak areas were measured for both solutions at time 0, 100 h and 150 h post preparation. Samples were stored at room temperature over the course of the analysis. Percentage change was calculated based on the peak area and compared to analysis at time zero. One replicate was analysed and 7.2 µl was injected (equivalent to 0.25 µg on column) for each sample. The concentration of the stock solutions assessed was 10 mM.

Column: Ascentis Express Peptide, ES-C18, 10 cm×4.6 mm

Mobile phases: 0.1% trifluoroacetic acid (TFA) in acetonitrile (organic) and 0.1% trifluoroacetic acid in water HPLC: Agilent 1260 infinity HPLC conditions used:

| Time (min) | Flow (ml) | Water + TFA | Acetonitrile + TFA |
|---|---|---|---|
| 0 | 1 | 90 | 10 |
| 2 | 1 | 90 | 10 |
| 8 | 1 | 0 | 100 |
| 9 | 1 | 90 | 10 |

Results:

At 100 hrs, the DMSO solution shows the Panobinostat concentration had decreased by 2.8%, whilst the citrate solution had decreased by 0.4%. Similarly, at 150 hrs the panobinostat in the DMSO solution had decreased by 4.4%, whereas the panobinostat in the citrate solution had decreased by only 1%.

| | Percentage relative to t = 0 | | |
|---|---|---|---|
| | 0 h | 100 h | 150 h |
| DMSO | 100 | 97.2 | 95.6 |
| Citrate | 100 | 99.6 | 99 |

Without wishing to be bound by any particular theory, the present inventors believe that the relatively lower stability of panobinostat in DMSO compared with that in the citrate solution may be caused by the oxidising nature of DMSO and its action on panobinostat. In light of this, it would be desirable to formulate panobinostat in a substantially DMSO-free solution.

A solution of HP-β-CD-Panobinostat in artificial CSF was prepared at an initial concentration of 40 µM panobinostat and several aliquots stored at 5° C. in upright sealed vials. Samples were taken at various time points (t=0, day 1, day 8, day 18 and day 22) and the panobinostat concentration measured by HPLC. The remaining panobinostat is expressed at a percentage of the starting concentration at t=0. The results were:

| Day | Panobinostat conc. |
|---|---|
| 0 | 100% |
| 1 | >99% |
| 8 | >99% |
| 18 | >99% |
| 22 | >99% |

At all of the time points measured, up to and including 22 days, the concentration of panobinostat was essentially unchanged: greater than 99% of the initial concentration. These results demonstrate that the HP-β-CD-Panobinostat formulated in artificial CSF is remarkably stable.

Example 5—Human DIPG Patient Treatment with RP-β-CD Panobinostat Via CED

A single patient (5 year old female) with DIPG was treated by direct CED infusion of HP-β-CD-panobinostat in artificial CSF.

The patient had a pre-implanted drug delivery system that incorporates a skull mounted transcutaneous port, which allows repeated administration of drug via CED.

HP-β-CD-panobinostat in artificial CSF was prepared as described above. HP-β-CD-panobinostat at a concentration of 10 µM was infused/convected over a period of about 8 hours for a total infused volume of 12 mL distributed over four catheters. Consultant-led paediatric anaesthetic care was provided. Continuous physiological monitoring was present, and hourly assessment of neurological function was obtained. This included accurate recording of limb and cranial nerve function.

The administration of HP-β-CD-panobinostat in artificial CSF via CED was found to be well-tolerated and no adverse events were observed.

Example 6—Lyophilisation of HP-β-CD-panobinostat Adduct

Two batches of the HP-β-CD-panobinostat adduct were produced according to the method set out in Example 1.

The first batch was released and laid down at 4° C. for long-term stability testing. At day 42, visible particles were observed in many vials of the product (but not all). Analysis of these particles showed them to contain only inorganic salts (i.e. they did not contain either the cyclodextrin or the panobinostat compound). Analysis by Energy-dispersive X-ray spectroscopy (EDX) showed the presence of magnesium and phosphorus, hence it was concluded that the visible particles were magnesium phosphate crystals.

Without wishing to be bound by any particular theory, the present inventors believe that the presence of an nanoparticulate form of cyclodextrin-adduct in artificial CSF (aCSF) may encourage nucleation of certain salts present in the aCSF. Artificial CSF contains a mixture of salts at varying concentrations. Some of these salts have intrinsically lower solubilities than others, hence are more likely to nucleate over time. The addition of a relatively large mass of cyclodextrin thought to be in an already-solid, nanoparticulate form, to the solution may well accelerate this nucleation.

The present inventors theorised that an improvement could be brought about by introducing a lyophilisation step. That is, by minimising the time these lower solubility salts spend in solution with the HP-β-CD-panobinostat adduct, i.e. by reconstituting just before administration, the inventors expect to circumvent the problem of gradual crystallisation of inorganic salts.

In the present example, the lyophilisation process involved cooling the samples containing HP-β-CD-panobinostat adduct to −52° C. under a vacuum (0.053 mbar) for around 2 hrs. However, other lyophilisation procedures are contemplated provided that they yield a substantially desiccated solid (e.g. water content below 10% w/w, below 5% w/w, or even below 2% w/w). The skilled person will be aware of numerous freeze-drying processes that will find use in connection with the present invention.

The modified process for production of HP-β-CD-panobinostat adduct in artificial CSF, in which the HP-β-CD-panobinostat adduct is lyophilised for storage/shipping prior to reconstitution in aCSF at the time of delivery to give a ready-to-inject solution, is set forth below.

Solution A: 0.1M Citric Acid in Water

Citric acid (Sigma Aldrich C-0759; Lot #21K0042) (2.101 g) was weighed out and dissolved in 100 mL ultrapure water.

Solution B: 0.1M Sodium Citrate in Water

Sodium citrate (tribasic) (Sigma Aldrich C3434; Lot #1304640/41807230 (2.944 g) was weighed out and dissolved in 100 mL ultrapure water.

Solution C: 0.1M Citrate Buffer

Solution A (82 mL) and solution B (18 mL) were added to a 250 mL Duran flask and mixed briefly to form [C]. The pH of the citrate buffer was measured and found to be pH3.0.

Solution D: 10 mM Panobinostat Solution in Citrate Buffer (25 mL)

Concentration=10 mM=0.01M
Volume=25 mL=0.025 L
Therefore number of moles required=$2.5 \times 10^{-4}$
Molecular weight of Panobinostat=349.43 g/mol
Therefore mass of Panobinostat required=82.36 mg
Thus, Panobinostat free base (81.0 mg) was weighed out and dissolved in solution C (24.59 mL).

The mixture was shaken on an orbital shaker for 10 minutes to give a clear, colourless solution [D].

Solution E: 100 mg/mL 2-Hydroxypropyl-β-Cyclodextrin in Water (20 mL)

2-Hydroxypropyl-β-cyclodextrin has an average molecular weight of 1460 g/mol. For simplicity it was prepared as follows.

Concentration=100 mg/mL. 2-Hydroxypropyl-β-cyclodextrin (Sigma Aldrich H107; Lot #048K0672) (2.004 g) was weighed out and dissolved in 20.04 mL ultrapure water. The mixture was shaken on an orbital shaker for 10 minutes to give a clear, colourless solution [E].

Solution F: Panobinostat—2-Hydroxypropyl-β-Cyclodextrin Adduct (5 mM)

Equal volumes of solutions D (2 mL) and E (2 mL) were mixed in a Falcon tube. The clear, colourless solution was vortexed briefly to homogenise.

Solution G: Panobinostat—2-Hydroxypropyl-β-Cyclodextrin Adduct (3.125 mM)

To produce a neutral solution (~pH7), a sample of [F] (1 mL) was mixed with NaOH$_{(aq)}$ (0.6 mL, 0.2M) to give a clear, colourless solution (1.6 mL in volume).

Lyophilised Solution G: 2 mL of adduct Solution G was lyophilised by cooling to −52° C. under a vacuum (0.053 mbar) for around 2 hrs to produce a solid cake. The lyophilised solid may then be stored as necessary, e.g. for shipping to a site of delivery.

Solution H: Sterile Solution of Panobinostat—2-Hydroxypropyl-β-Cyclodextrin Adduct in aCSF (Artificial Cerebrospinal Fluid) (40 μM)

The lyophilised solid cake from 2 mL of solution G above was reconstituted by adding 10 mL of aCSF to give a 40 μM solution of Panobinostat in aCSF. This solution may be further diluted according to the dosage or volume that is required for the treatment.

Example 7—Long-Term Storage Stability of HP-β-CD-Panobinostat Adduct

The long-term stability of the HP-β-CD-panobinostat adduct was assessed by measuring panobinostat concentration and percentage impurities at intervals from t=0 to a total of 24 weeks stored at −25° C.--15° C. (data not shown), 2° C.-8° C. (data not shown), and 15° C.-25° C. (FIGS. 3 and 4).

Figure 3:
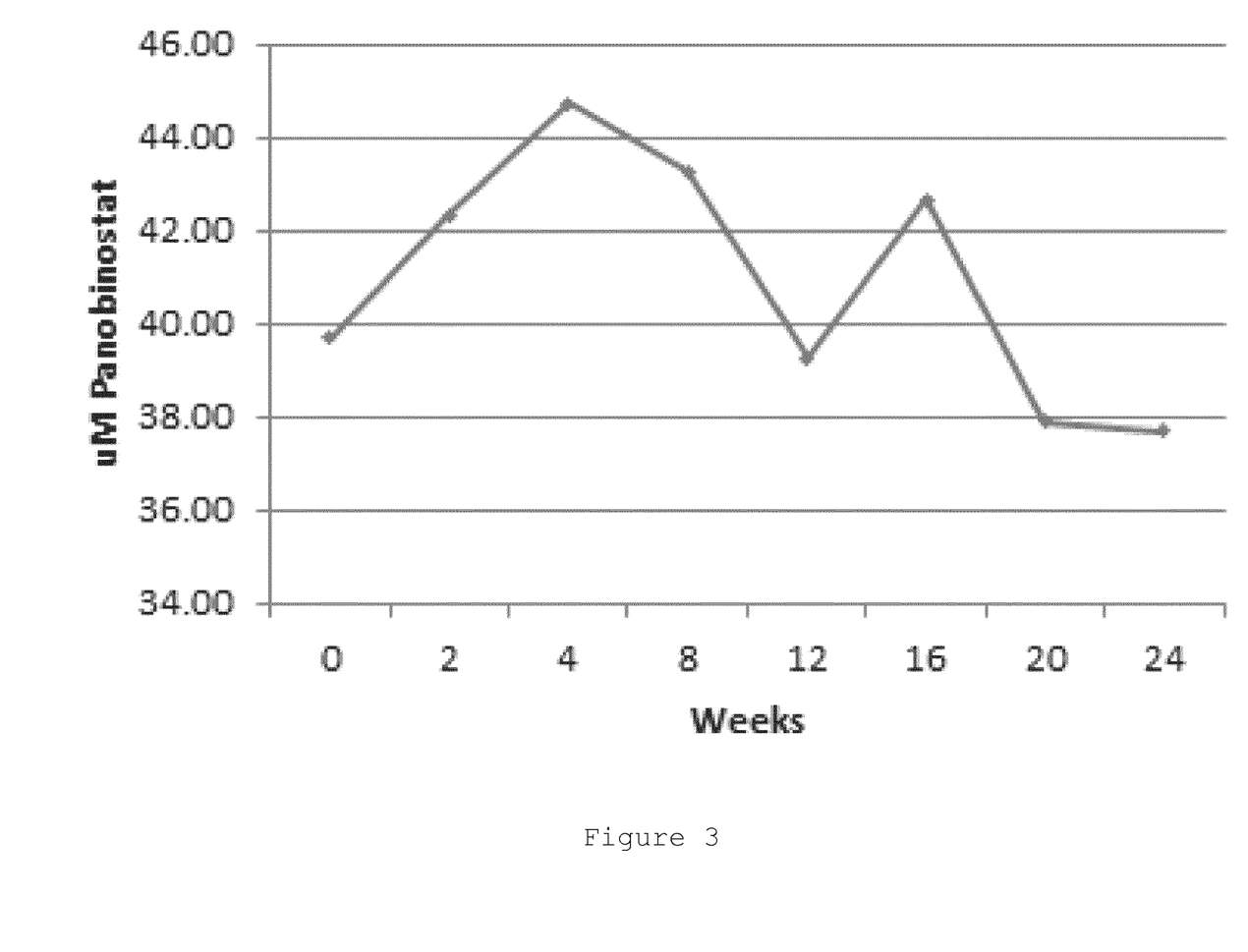
FIG. 3 shows panobinostat concentration (μM) over time for a 24-week storage test at 15° C.-25° C. The measured panobinostat concentration of the stored HP-β-CD panobinostat adduct was remarkably stable even out to the full 24-week period of the study.

As shown in FIG. 3, panobinostat concentration was found to be very stable over the 24-week period at 15° C.-25° C. The equivalent concentrations plots for −25° C.--15° C. and 2° C.-8° C. also showed a similar profile with measured concentration remaining within the range 38 μM to 45 μM.

Figure 4:
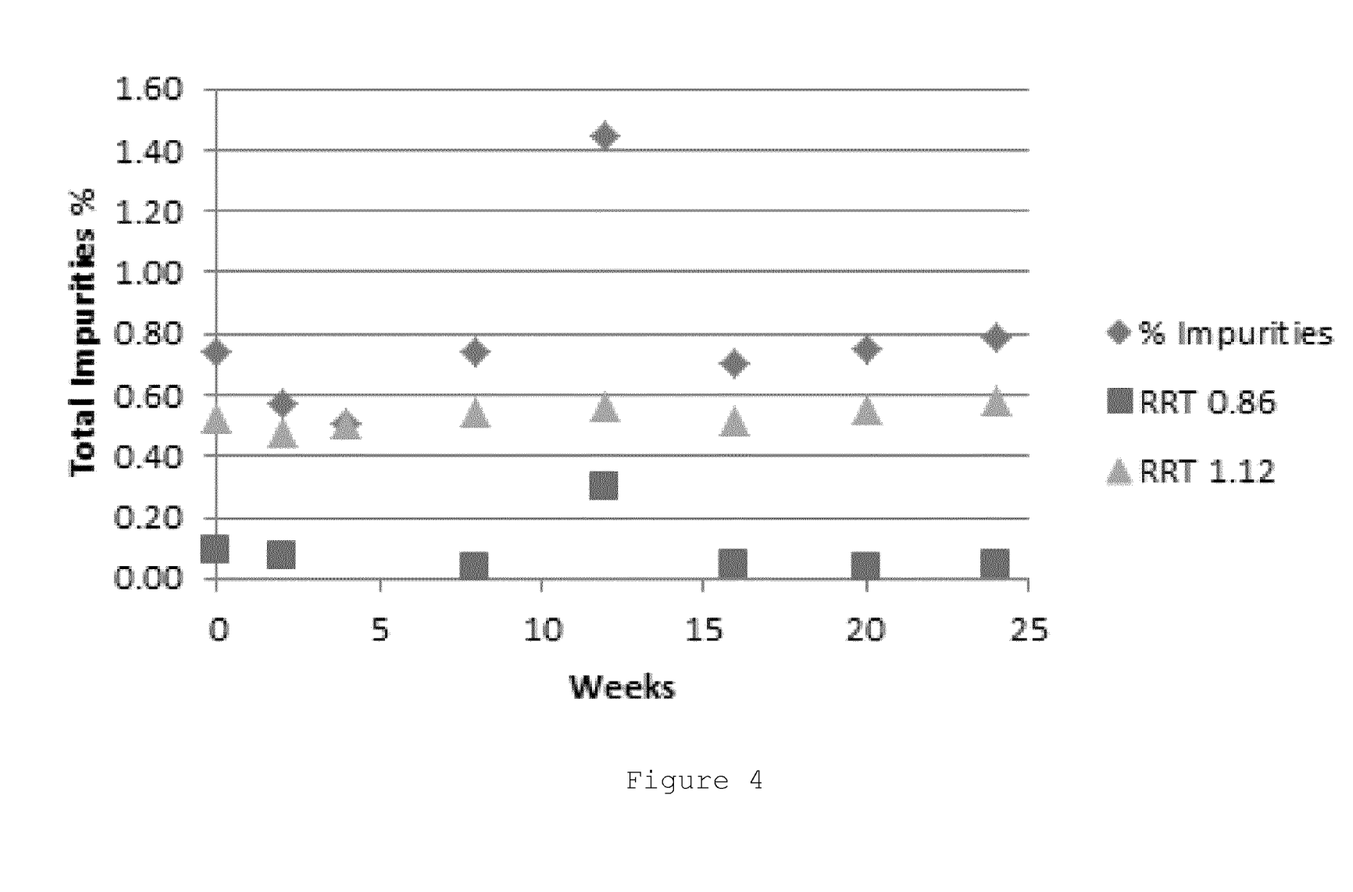
FIG. 4 shows total impurities (diamonds) as a percentage plotted against time for a 24-week storage test at 15° C.-25° C. Relative retention time (RRT) 0.86 (squares) and RRT 1.12 (triangles) refer to chromatogram peaks either side of the main panobinostat drug peak. The plot shows that the RRT peaks and total % impurities remained stable and low throughout the study period implying that formation of panobinostat degradation products is negligible.

Possible degradation of panobinostat over time at 15° C. to 25° C. was assessed by measuring peaks either side of the main panobinostat compound peak by HPLC (see RRT 0.86 and RRT 1.12 in FIG. 4). Total impurities as a percentage are also shown on FIG. 4. The FIG. 4 plots show that impurities remained at a very low level (around 1% or less) for the 24-week duration of the study. Very similar results were seen for storage at −25° C.--15° C. and 2° C.-8° C. over the same time period.

Taken together, the panobinostat concentration and impurity measurements indicate that the HP-β-CD-panobinostat adduct is stable even at room temperature over a period of at least up to 24 weeks.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A method for producing a cyclodextrin-panobinostat adduct having a concentration of less than 1000 parts per million (ppm) of acetone, tetrahydrofuran, dichloromethane, acetonitrile, dimethylformamide and dimethyl sulphoxide (DMSO),comprising:

a) providing a first aqueous solution comprising a buffering agent, the solution having a pH in the range 2.0 to 4.0;

b) dissolving panobinostat in said first aqueous solution to provide a second aqueous solution;

c) mixing said second aqueous solution comprising panobinostat with a third aqueous solution comprising a cyclodextrin to form a fourth aqueous solution comprising a cyclodextrin-panobinostat adduct; and d) adding a sufficient quantity of a base to said fourth aqueous solution comprising the cyclodextrin-panobinostat adduct in order to provide a fifth aqueous solution having a pH in the range 6.0 to 8.0.

2. The method according to claim 1, wherein:

the cyclodextrin is 2-hydroxypropyl-β-cyclodextrin; and/or the buffering agent comprises citric acid and citrate.

3. The method according to claim 1, further comprising drying said fifth aqueous solution to form a solid comprising said cyclodextrin-panobinostat adduct.

4. The method according to claim 3, wherein said drying comprises freeze-drying under reduced pressure to form a lyophilised solid comprising said cyclodextrin-panobinostat adduct.

5. The method according to claim 3, wherein said solid has a water content of less than 10% w/w.

6. The method according to claim 3, further comprising reconstituting said solid by dissolving in a reconstitution solution.

7. The method according to claim 6, wherein the reconstitution solution comprises: artificial cerebrospinal fluid (CSF), Ringer's solution, water for injection (WFI), or a buffered salt solution.

8. The method according to claim 7, wherein the reconstitution solution comprises artificial CSF.

9. The method according claim 7, further comprising adjusting the pH of the solution before, during or after reconstitution.

10. The method according to claim 1, further comprising mixing said fifth aqueous solution comprising the cyclodextrin-panobinostat adduct with an artificial cerebrospinal fluid (CSF) solution to provide a sixth aqueous solution comprising the cyclodextrin-panobinostat adduct in artificial CSF.

11. The method according to claim 8, wherein the concentration of panobinostat in the artificial CSF is in the range 1 μM to 20 μM.

12. The method according to claim 1, further comprising the step of filtering and/or sterilizing at least one of said solutions and/or said solid comprising said cyclodextrin-panobinostat adduct.

13. The method according to claim 8, further comprising introducing at least a portion of the cyclodextrin-panobinostat adduct in artificial CSF into at least one convection-enhanced delivery (CED) catheter.

* * * * *